US008043235B2

(12) United States Patent
Schwartz

(10) Patent No.: US 8,043,235 B2
(45) Date of Patent: *Oct. 25, 2011

(54) ULTRASONIC TREATMENT OF GLAUCOMA

(76) Inventor: Donald N. Schwartz, Long Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/713,122

(22) Filed: Feb. 25, 2010

(65) Prior Publication Data
US 2010/0152626 A1 Jun. 17, 2010

Related U.S. Application Data

(63) Continuation-in-part of application No. 11/842,909, filed on Aug. 21, 2007, now Pat. No. 7,909,781.

(60) Provisional application No. 60/839,473, filed on Aug. 22, 2006.

(51) Int. Cl.
A61F 9/007 (2006.01)
A61B 18/00 (2006.01)
A61B 18/04 (2006.01)

(52) U.S. Cl. .................... 601/2; 606/27; 606/28
(58) Field of Classification Search .................. 601/2
See application file for complete search history.

(56) References Cited

U.S. PATENT DOCUMENTS

| 4,350,917 A | 9/1982 | Lizzi |
| 4,484,569 A | 11/1984 | Driller |
| 4,531,934 A | 7/1985 | Kossovsky |
| 4,561,019 A | 12/1985 | Lizzi |
| 4,729,373 A | 3/1988 | Peyman |
| 4,858,124 A | 8/1989 | Lizzi |
| 5,080,101 A | 1/1992 | Dory |
| 5,209,221 A | 5/1993 | Riedlinger |
| RE34,663 E * | 7/1994 | Seale ............... 600/587 |
| 5,458,130 A | 10/1995 | Kaufman |
| 5,636,635 A * | 6/1997 | Massie et al. ......... 600/405 |
| 5,865,742 A * | 2/1999 | Massie ................ 600/405 |
| 6,039,689 A | 3/2000 | Lizzi |
| 6,162,193 A | 12/2000 | Ekberg |
| 6,352,519 B1 | 3/2002 | Anis |
| 6,416,740 B1 | 7/2002 | Unger |

(Continued)

FOREIGN PATENT DOCUMENTS
FR 2631545 A1 11/1989
(Continued)

OTHER PUBLICATIONS

F. Valot et al., Treatment of glaucoma with high intensity focused ultrasound, International Opthalmology 13: 167-170 (1989).*

(Continued)

Primary Examiner — Roy Gibson
Assistant Examiner — Kaitlyn Smith
(74) Attorney, Agent, or Firm — Jeffer Mangels; Butler & Mitchell LLP

(57) ABSTRACT

A method of treating glaucoma is described herein. The method includes the steps of providing an ultrasonic device that emits ultrasonic energy, holding the ultrasonic device at a location external to the trabecular meshwork, transmitting the ultrasonic energy at a frequency to a desired location for a predetermined time, causing biochemical changes to be initiated within the eye that may include triggering a presumed integrin response that initiates biochemical changes typified by but not limited to cytokines, enzymes, macrophage activity and heat shock proteins, and dislodging material built up in the trabecular meshwork.

12 Claims, 8 Drawing Sheets

U.S. PATENT DOCUMENTS

| | | | | |
|---|---|---|---|---|
| 6,433,464 | B2* | 8/2002 | Jones | 310/328 |
| 6,544,254 | B1* | 4/2003 | Bath | 606/6 |
| 6,576,875 | B1* | 6/2003 | Kleffner et al. | 219/494 |
| 6,618,620 | B1* | 9/2003 | Freundlich et al. | 607/27 |
| 6,652,459 | B2 | 11/2003 | Payne | |
| 6,679,855 | B2 | 1/2004 | Horn | |
| 6,685,657 | B2 | 2/2004 | Jones | |
| 6,764,439 | B2 | 7/2004 | Schaaf | |
| 6,979,328 | B2 | 12/2005 | Baerveldt | |
| 7,083,591 | B2* | 8/2006 | Cionni | 604/31 |
| 7,094,225 | B2 | 8/2006 | Tu | |
| 7,104,958 | B2* | 9/2006 | Crutchfield et al. | 600/454 |
| 2001/0014780 | A1 | 8/2001 | Martin et al. | 601/2 |
| 2002/0039594 | A1* | 4/2002 | Unger | 424/426 |
| 2002/0111608 | A1 | 8/2002 | Baerveldt | |
| 2002/0159952 | A1* | 10/2002 | Unger | 424/9.51 |
| 2003/0088260 | A1 | 5/2003 | Smedley | |
| 2003/0097151 | A1 | 5/2003 | Smedley | |
| 2004/0030269 | A1 | 2/2004 | Horn | |
| 2004/0049105 | A1* | 3/2004 | Crutchfield et al. | 600/407 |
| 2004/0050392 | A1* | 3/2004 | Tu et al. | 128/898 |
| 2004/0091541 | A1 | 5/2004 | Unger | |
| 2005/0249667 | A1* | 11/2005 | Tuszynski et al. | 424/9.3 |
| 2006/0047263 | A1 | 3/2006 | Tu | |
| 2006/0106370 | A1 | 5/2006 | Baerveldt | |
| 2006/0106424 | A1 | 5/2006 | Bachem | |
| 2006/0173437 | A1 | 8/2006 | Robin | |
| 2006/0217741 | A1 | 9/2006 | Ghannoum | |
| 2008/0051680 | A1* | 2/2008 | Luebcke | 601/2 |
| 2008/0177220 | A1* | 7/2008 | Lindgren et al. | 604/22 |
| 2008/0286255 | A1* | 11/2008 | Schwartz et al. | 424/94.1 |
| 2010/0152626 | A1* | 6/2010 | Schwartz | 601/2 |
| 2010/0260669 | A1* | 10/2010 | Yun et al. | 424/1.49 |
| 2011/0077626 | A1* | 3/2011 | Baerveldt et al. | 606/6 |
| 2011/0081333 | A1* | 4/2011 | Shantha et al. | 424/94.62 |
| 2011/0092781 | A1* | 4/2011 | Gertner | 600/301 |
| 2011/0092880 | A1* | 4/2011 | Gertner | 604/20 |
| 2011/0118600 | A1* | 5/2011 | Gertner | 600/439 |

FOREIGN PATENT DOCUMENTS

| | | |
|---|---|---|
| WO | 2006021651 A1 | 3/2006 |

OTHER PUBLICATIONS

C.C. Sterk et al., The effect of therapeutic ultrasound on the average of multiple intraocular pressures throughout the day in therapy-resistant glaucoma, Graefe's Arch Clin Exp Opthalmol (1989) 227; 36-38.*

Extended European Search Report dated Sep. 10, 2009, which includes the supplementary European search report and the European search opinion, for related European Application No. 07814316.1.

Wang N, Chintala SK, Fini ME, Schuman JS; Ultrasound activates the TM ELAM-1/IL-1/NF-kappaB response: a potential mechanism for intraocular pressure reduction after phacoemulsification; Invest Ophthalmol Vis Sci. May 2003; 44(5):1977-81.

Bradley JM, Anderssohn AM, Colvis CM, Parshley DE, Zhu XH, Ruddat MS, Samples JR, Acott TS; Mediation of laser trabeculoplasty-induced matrix metalloproteinase expression byIL-1 and TNF; Invest Ophthalmol Vis Sci. 2000; 41:422-430.

Hosseini M, Rose AY, Song K, Bohan C, Alexander JP, Kelley MJ, Acott TS; IL-1 and TNF induction of matrix metalloproteinase-3 by c-Jun N-terminal kinase in trabecular meshwork; Invest Ophthalmol Vis Sci. Apr. 2006; 47(4):1469-76.

Pang IH, Hellberg PE, Fleenor DL, Jacobson N, Clark AF; Expression of matrix metalloproteinases and their inhibitors in human trabecular meshwork cells; Invest Ophthalmol Vis Sci. Aug. 2003; 44(8):3485-93.

Alexander JP, Acott TS; Involvement of the Erk-MAP kinase pathway in TNFalpha regulation of trabecular matrix metalloproteinases and TIMPs; Invest Ophthalmol Vis Sci. Jan. 2003; 44(1):164-9.

Kelley MJ, Rose A, Song K, Lystrup B, Samples JW, Acott TS; p38 MAP kinase pathway and stromelvsin regulation in trabecular meshwork cells; Invest Ophthalmol Vis Sci. Jul. 2007; 48(7):3126-37.

Kelley MJ, Rose AY, Song K, Chen Y, Bradley JM, Rookhuizen D, Acott TS; Synergism of TNF and IL-1 in the induction of matrix metalloproteinase-3 in trabecular meshwork; Invest Ophthalmol Vis Sci. Jun. 2007;48(6):2634-43.

Office Action issued on May 25, 2010, by Chinese Intellectual Property Office in related Chinese Patent Application No. 200780035161.2.

Luna C, Li G, Liton PB, Qiu J, Epstein DL, Challa P, Gonzalez P; Resveratrol prevents the expression of glaucoma markers induced by chronic oxidative stress in trabecular meshwork cells; Food Chem Toxicol. Jan. 2009; 47(1):198-204. Epub Nov. 6, 2008.

Alexander JP, Acott TS; Involvement of protein kinase C in TNFalpha regulation of trabecular matrix metalloproteinases and TIMPs; Invest Ophthalmol Vis Sci. Nov. 2001; 42(12):2831-8.

Fleenor DL, Pang IH, Clark AF; Involvement of AP-1 in interleukin-1alpha-stimulated MMP-3 expression in human trabecular meshwork cells; Invest Ophthalmol Vis Sci. Aug. 2003;44(8):3494-501.

Written Opinion issued in related Singapore Application No. 200901271-7, provided by the Austrian Patent Office as Search and Examination Authority, with a mailing date of May 19, 2010.

Bradley, John M.B., et al., "Effects of Mechanical Stretching on Trabecular Matrix Metalloproteinases", Investigative Ophthalmology & Visual Science, Jun. 2001, vol. 42 No. 7.

"Cellular Tolerance to Pulsed Hyperthermia", by D. M. Simanovskii, et al., Physical Review, Jul. 24, 2006.

Effect of Ultraviolet Irradiation Upon the Cutaneous Pain Threshold, by M. Lipkin, et al., Journal of Applied Physiology May 1955 vol. 7 No. 6 683-687.

"Cytokine induction by 41.8°C whole body hyperthermia", by H. Ian Robins, et al., Cancer Letters, vol. 97, Issue 2, Nov. 6, 1995, pp. 195-201.

"Stress Induced Changes in Lymphocyte Subpopulations and Associated Cytokines During Whole Body Hyperthermia of 41.8-42.2°C" O. Ahlers, et al., Eur J Appl Physiol (2005) 95: 298-306.

"Heat Shock Proteins and Regulation of Cytokine Expression", by Y. Xie, C.M. Cahill, A. Asea, P.E. Auron, and S.K. Calderwood, Infectious Diseases in Obstetrics and Gynecology 7:26-30 (1999).

"Effects of Local and Whole Body Hyperthermia on Immunity", by Gian Franco Baronzio, et al. can be found in the Madame Curie Bioscience Database [Internet], Austin (TX): Landes Bioscience; 2000. It can be found on the Internet at http://www.ncbi.nlm.nih.gov/books/NBK6083/.

"Heat Shock Co-Activates Interleukin-8 Transcription", by Ishwar S. Singh, et al., Am J Respir Cell Mol Biol, Aug. 2008; 39(2): 235-242.

Preliminary Amendment dated Jun. 5, 2009, filed in related U.S. Appl. No. 11/842,909.

Office Action dated Jan. 12, 2010, issued in in related U.S. Appl. No. 11/842,909.

Amendment/Response to Office Action dated Mar. 16, 2010, filed in related U.S. Appl. No. 11/842,909.

Final Office Action dated Jun. 11, 2010, issued in in related U.S. Appl. No. 11/842,909.

Examiner's Interview Summary dated Dec. 7, 2010, issued in in related U.S. Appl. No. 11/842,909.

Amendment/Response to Office Action dated Dec. 9, 2010, filed in related U.S. Appl. No. 11/842,909.

* cited by examiner

ULTRASONIC TREATMENT OF GLAUCOMA

This application is a continuation-in-part of U.S. patent application Ser. No. 11/842,909 now U.S. Pat. No. 7,909,781, filed on Aug. 21, 2007, which claims the benefit of U.S. Provisional Application No. 60/839,473, filed Aug. 22, 2006, which are both incorporated by reference herein in their entireties.

FIELD OF THE INVENTION

The present invention relates generally to the treatment of glaucoma and, more particularly, to a method for treatment of glaucoma using, low intensity ultrasonic energy.

BACKGROUND OF THE INVENTION

Open angle glaucoma exists when the pressure in the eye is not tolerated by the patient and is causing damage to the optic nerve. The current treatment for open angle glaucoma is aimed at reducing the intraocular pressure to a level that is safe for the patient's eye, to preserve vision.

Open angle glaucoma is treated with pharmaceutical agents. Another method of treatment, laser treatment for open angle glaucoma, has been reserved for medical treatment failures but is gaining some favor as a primary treatment. Another approach, intraocular surgery, is reserved for medical and/or laser failures.

Frequently, the increased pressure in the eye is caused by a blockage in the ability of the fluid to leave the eye, not an actual increase of the fluid itself. As shown in FIG. 1, the blockage is typically in the part of the trabecular meshwork near Schlemm's canal, called the juxtacanalicular meshwork. The meshwork is typically blocked by anatomical changes, pigment, extracellular matrix debris or pseudoexfoliative material.

Medical treatment is directed at decreasing the production of the fluid (aqueous humor) or enhancing the ability of the fluid to leave the eye. Medical treatment is not curative. It is used on a continuing basis to decrease the pressure. But, when the treatment is stopped the pressure rises. Also, medical treatment demands patient compliance, has unwanted side effects, is expensive, and may interact poorly with other medical care for the patient.

Laser treatment has been partially successful in its original (argon) method. Newer laser treatment, such as selective laser trabeculoplasty, is gaining favor. However, laser treatment is performed on the inside of the eye and treats the inner, not the outer, trabecular meshwork. With this treatment, there is a secondary physiologic response that leads to an increase in fluid outflow after the laser is performed.

Frequently, after modern day cataract surgery there is a decrease in the intraocular pressure as an unintended positive side effect. Typical modern cataract surgery removes the cataract by ultrasonic emulsification of the lens material. This method is known as phacoemulsification. Older cataract surgery, without implants, removed more material from inside the eye, but the decrease in intraocular pressure was not as consistent as with modern day or current surgery. It is believed that the ultrasound used to break up the lens material helps dislodge the built up material. However, this is just a side effect, and, as described below, the ultrasonic energy used in phacoemulsification is intense enough to damage tissue.

Accordingly, a need exists for a treatment of glaucoma that includes a method of applying ultrasonic energy to the eye to dislodge built up material and initiate biochemical processes to reduce and remove extracellular debris, thereby decrease pressure, and that can be performed without damaging tissue.

SUMMARY OF THE PREFERRED EMBODIMENTS

In accordance with a first aspect of the present invention, there is provided a method of treating glaucoma. The method includes the steps of providing an ultrasonic device that emits ultrasonic energy, holding the ultrasonic device at a location external to the trabecular meshwork, transmitting the ultrasonic energy at a frequency to a desired location for a predetermined time, causing biochemical changes to be initiated within the eye that may include triggering a presumed integrin response that initiates biochemical changes typified by but not limited to cytokines, enzymes, macrophage activity and heat shock proteins, and dislodging material built up in the trabecular meshwork. In a preferred embodiment, the tip is rounded and flat.

In accordance with another aspect of the present invention, there is provided a handheld ultrasonic device that includes a casing, an ultrasonic transducer disposed in the casing, a power supply, a rod extending from the ultrasonic transducer, and a tip located at the end of the rod. Ultrasonic energy is transferred from the ultrasonic transducer to the tip. In a preferred embodiment, the casing is attached to the ultrasonic transducer at a null point.

In accordance with another aspect of the present invention, there is provided a method of treating glaucoma in a human eye that includes an intraocular lens with an exterior surface, a cornea, a sclera, and a trabecular meshwork. The method includes the steps of implantation of the intraocular lens, providing an ultrasonic device that emits ultrasonic energy, holding the ultrasonic device at a location spaced from the intraocular lens, transmitting the ultrasonic energy at a frequency to a desired location for a predetermined time, dislodging material built up in the trabecular meshwork, and generating heat that initiates biochemical changes within the eye.

The device disclosed herein preferably includes a metallic tip and focused ultrasound that is aimed at increasing/triggering integrins, and elevating the temperature within the treatment area to a level that begins a biochemical cytokine cascade that is then absorbed systemically leading to a decrease in intraocular pressure in both eyes.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Described herein are preferred embodiments of a method for the ultrasonic treatment of glaucoma. The method includes the use of tools that are also shown in FIGS. 3-6.

Generally, the method includes providing ultrasonic energy to a desired area of the eye to dislodge and/or remove material from the trabecular meshwork, thereby lowering the pressure within the eye. The presently described methods are used to reduce the pressure build up in the eye described above.

It will be appreciated that terms such as "front," "back," "top," "bottom," "side," "upwardly" and "downwardly" used herein are merely for ease of description and refer to the orientation of the components as shown in the figures. It should be understood that any orientation of the instruments and the components thereof described herein is within the scope of the present invention.

Figure 2:
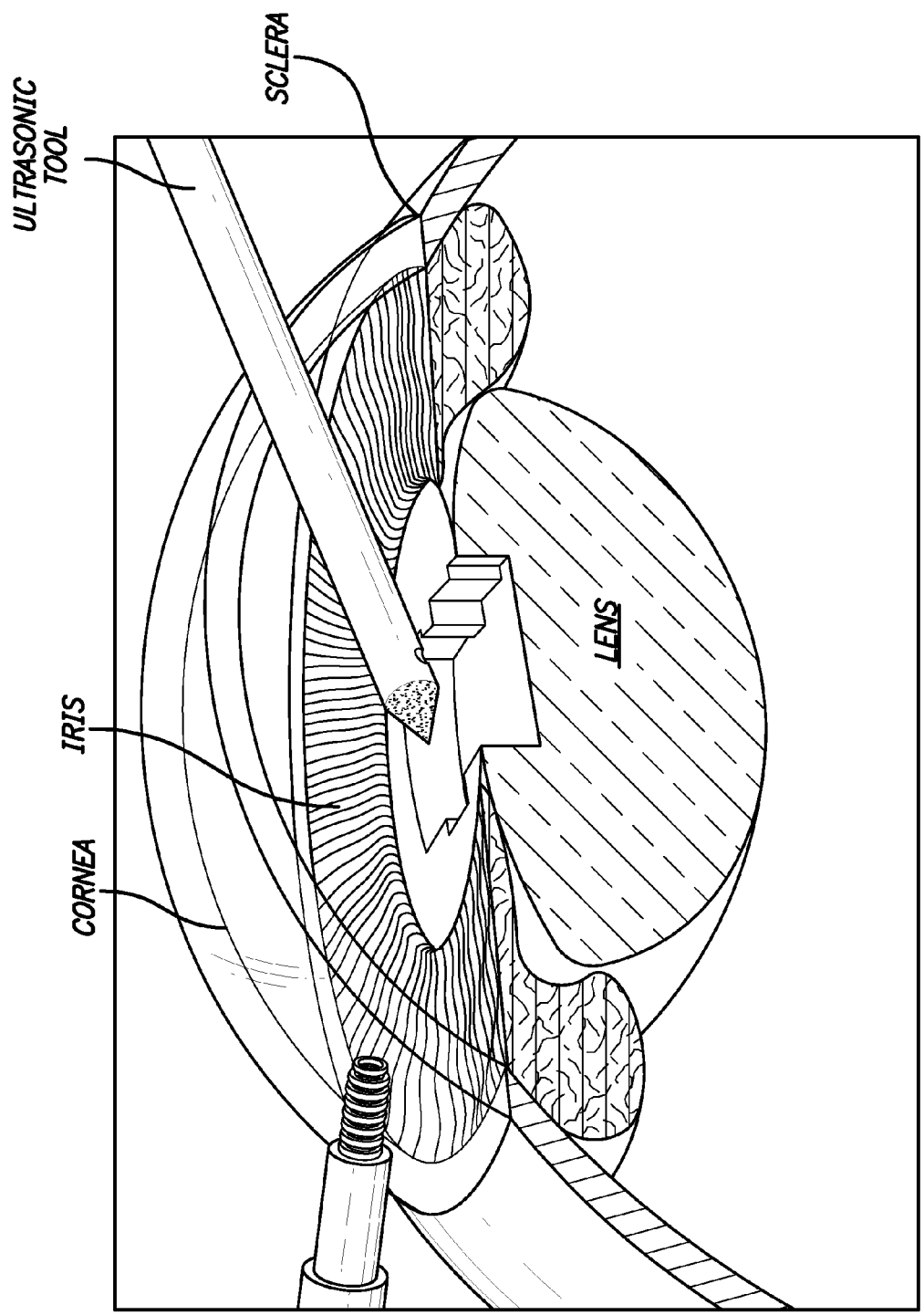
FIG. 2 is a view of a portion of the inside of an eye that includes instruments used in phacoemulsification.

FIG. 2 shows phacoemulsification being performed on an eye. As is described, the technique of phacoemulsification has been shown to cause a decrease of pressure in the eye. However, the ultrasound intensity used in phacoemulsification is quite vigorous and is designed to carve the lens tissue or disrupt its anatomy. As can be seen in FIG. 2, the instrument is actually in contact with the lens. In addition, the commonly used ultrasound instrument for phacoemulsification has a tip that is pointed and sharp, is designed to engage the tissue in the eye directly and has three inputs for ultrasound, irrigation and aspiration.

In a preferred embodiment of the present invention, the instruments (described below) focus the energy of the ultrasound a distance from the tissue and do not engage it directly.

Moreover, the ultrasound intensity is preferably significantly less vigorous than phacoemulsification and, therefore, creates acoustic energy at a much gentler intensity. Lastly, the specific area and focus of the treatment is the anterior chamber angle including the ciliary body and trabecular meshwork in the anterior portion of the globe, and not the crystalline lens of the eye, as in phacoemulsification.

The forces obtained from ultrasound treatment are complex, but an fit into three categories: sonomechanical, heat generated and integrin triggering. For example, see U.S. patent application Ser. No. 11/220,128 to Bachem and U.S. Pat. No. 6,162,193 to Ekberg, the entireties of which are incorporated herein by reference. Ultrasound creates microbubbles which may implode vigorously and thereby create heat and violent micromovement. This is known as cavitation. This creation of microbubbles and subsequent implosion with heat is either stable or unstable (transient). The stable cavitation is less likely to lead to cell necrosis and tissue damage. In addition there is an effect of the wavefront of the ultrasound that creates a phenomenon of streaming that allows the movement of particles within a fluid.

The device 10 for the treatment of glaucoma by ultrasound described below includes a balance such that the frequency, power and duration of the propagated ultrasound has the optimum balance of controlled cavitation, heat and acoustic streaming to effect the trabecular meshwork. The effect is such that debris, or other occlusive structures, may be dislodged to create a larger outflow by the forces mentioned above. In addition the nature of the heat generated and the subsequent inflammatory reaction and integrin absorption of ultrasound with the release of cytokines is directed to initiating cascades of biochemical reactions that lead to remodeling of the extracellular matrix and induction of macrophages to remove extracellular debris to further enhance the long term effect of the treatment. It will be understood that performance of the method described herein causes an inflammatory response that causes the cells to release cytokines. The cytokines trigger enzymes and macrophage activity. The enzymes break down the extracellular debris clogging the trabecular meshwork and the macrpophages clear the broken down debris.

Described herein are two types of instruments used for ultrasonically treating the eye, one for immediately after cataract surgery (intraocular), and one for use on the surface of the eye (external), which can be used without having to enter the interior of the eye.

Figure 3:
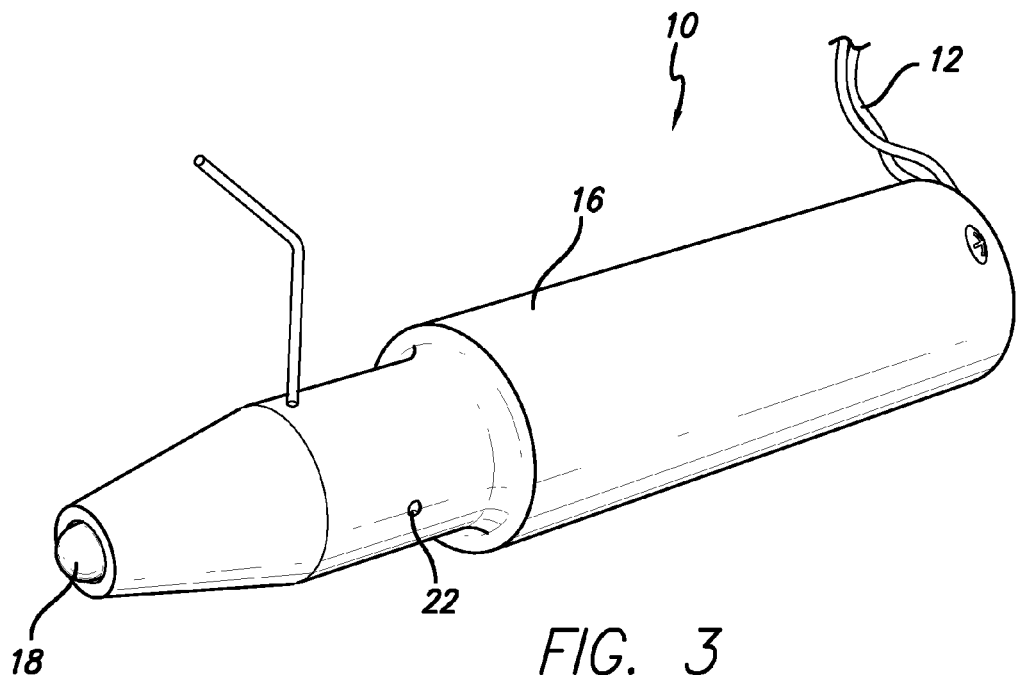
FIG. 3 is a perspective view of an ultrasonic device used for treatment of glaucoma that is used external of the eye, in accordance with a preferred embodiment of the present invention.
Figure 4:
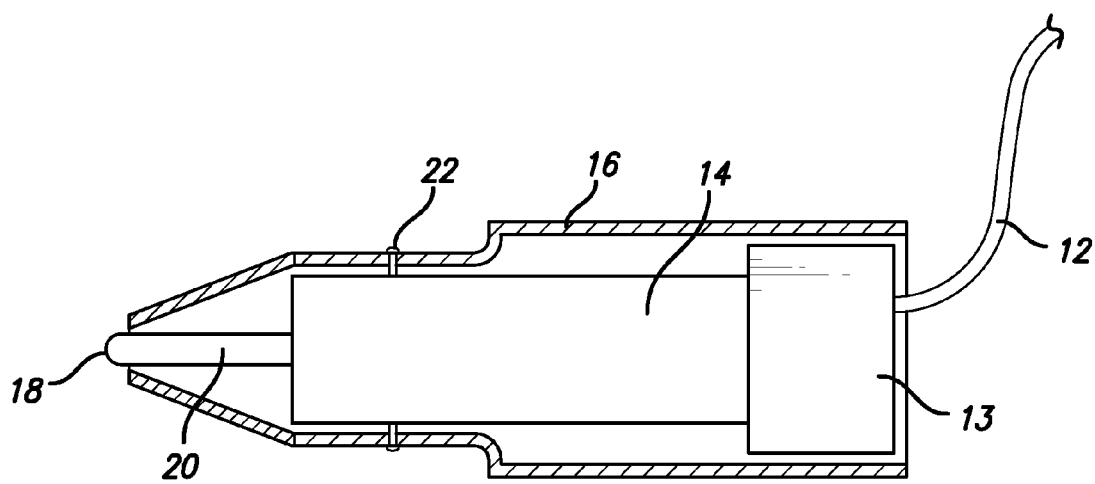
FIG. 4 is a cross-sectional side elevational view of the device of FIG. 3.
Figure 5:
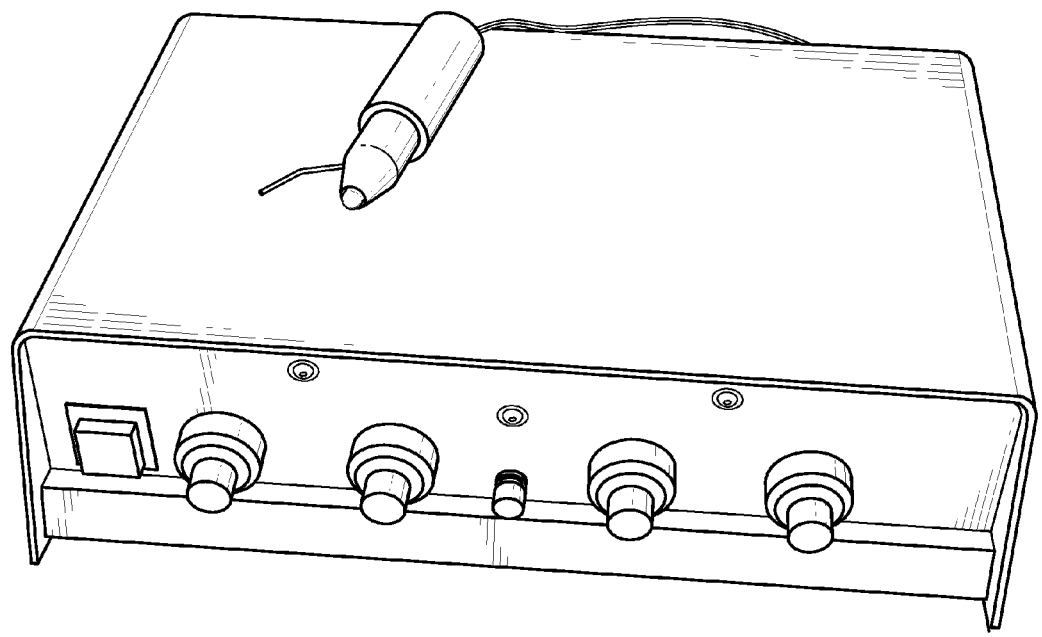
FIG. 5 a perspective view of the ultrasonic device of FIG. 3 along with a power supply.
Figure 7:
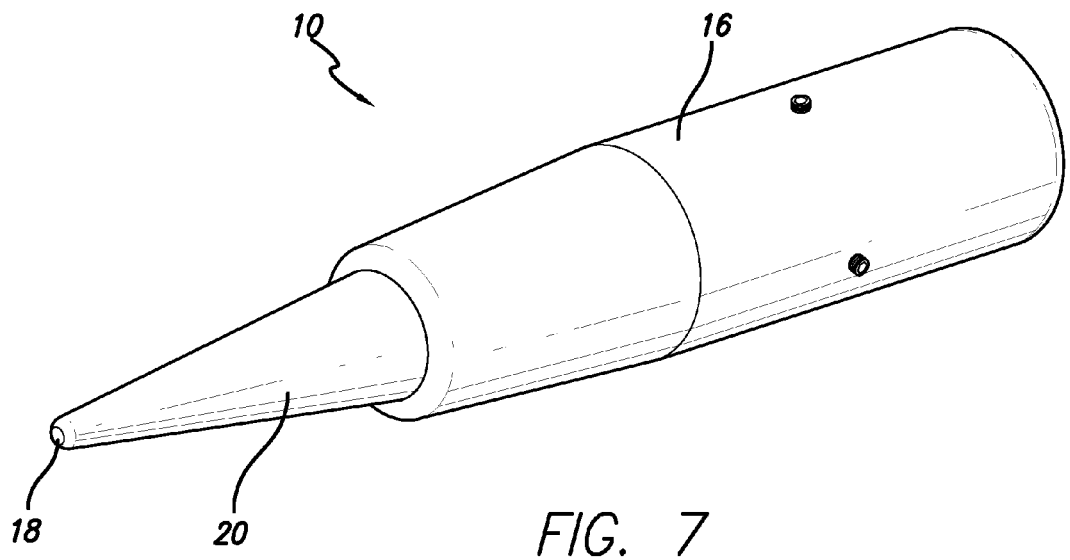
FIG. 7 is a perspective view of an ultrasonic device used for treatment of glaucoma that is used external of the eye, in accordance with another preferred embodiment of the present invention.
Figure 8:
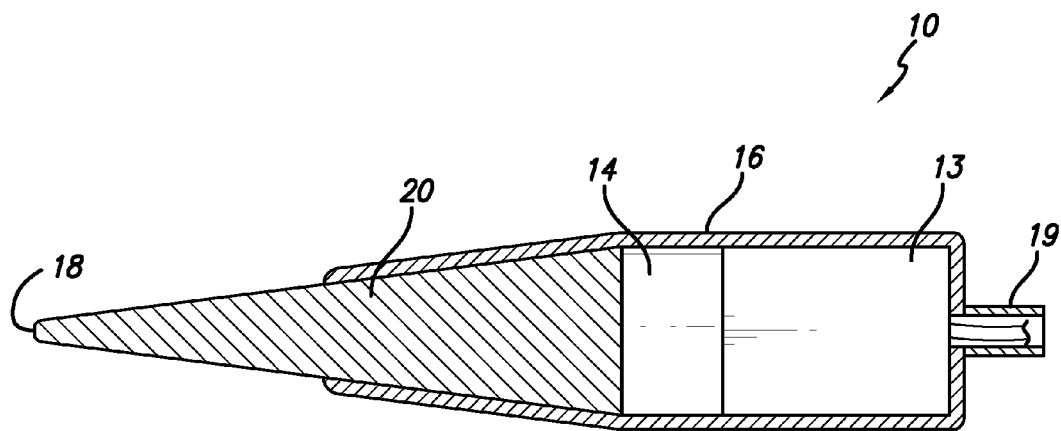
FIG. 8 is a cross-sectional side elevational view of the device of FIG. 7.

Referring to FIGS. 3-5, a device or probe 10 for treatment on the outside surface of the eye is shown. Generally, the device 10 includes a power cord 12, a power supply 13 and an ultrasonic transducer 14 housed within a casing 16. It is contemplated that either AC or DC power can be used. However, in a preferred embodiment, DC power is provided (which may be from alternating current and then converted to DC or it may be from a battery pack). It will be understood by those skilled in the art that the type of ultrasonic transducer is not a limitation on the present invention. For example, the ultrasonic energy can be provided by piezoelectrics, liquids, crystals, etc. See, for example, U.S. Pat. No. 6,616,030 to Miller, which is incorporated by reference in its entirety herein. In the example shown in the figures, the ultrasonic transducer 14 uses piezoelectric technology. The ultrasonic energy produced by the transducer 14 is transmitted down a rod 20 and to the tip 18. Preferably, the tip 18 is smooth and rounded with a surface that allows for appropriate gel or liquid interface to the ocular surface. The smooth tip is preferred over the sharp tip of the prior art to prevent laceration of the exterior ocular surface or the cornea. In another embodiment, as shown in FIGS. 7-8, the tip 18 is round or circular, but generally flat.

In a preferred embodiment, the casing 16 is attached to the transducer at a null point so as to not upset, or diminish ultrasound production within the casing; but avoiding contact with the tip to 18 allow maximum energy. As shown in FIG. 4, there is a space between the casing 16 and rod 20 and/or tip 18. The casing 16 can be attached to the transducer, for example, by threaded fasteners 22, rivets or the like.

As shown in FIGS. 3-5, the casing 16 has is shaped so that it fits easily into a user's hand. In a preferred embodiment, the casing 16 includes a handle 24 extending therefrom that can be grasped by a user's second hand. With this design the user can grasp the casing 16 with one hand and use the other hand to guide the device 10 using the handle 24. This provides a greater ability to manipulate the device 10 as desired. The handle 24 may be straight or bent (as is shown in FIG. 3). The casing 16 may also include a depression or depressions therein or other ergonomic additions to make the casing 16 easier to grip.

In an exemplary embodiment, the device is 9 cm long from the back of the casing to the tip and the tip is rounded to approximately a 4 mm diameter. However, this is not a limitation on the present invention.

Figure 4A:
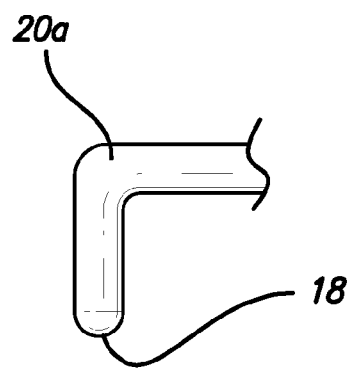
FIG. 4a is a side elevational detail of the tip of the device of FIG. 3 with a bent rod.

As shown in FIG. 4, in a preferred embodiment, the rod 20 is straight. However, in another embodiment, the rod 20 can be bent at an angle. As shown in FIG. 4a, the angle can be about 90 degrees. However, the angle can also be between 0 and 90 degrees. The ultrasonic energy is transmitted directly to the tip 18 and with the straight rod 20 provides movement in a forward and backward direction (like a piston or jackhammer). The rod 20a bent at a 90 degree angle provides for motion that is parallel to the axis of the rod and causes a back and forth sliding movement at the tip 18.

Figure 4B:
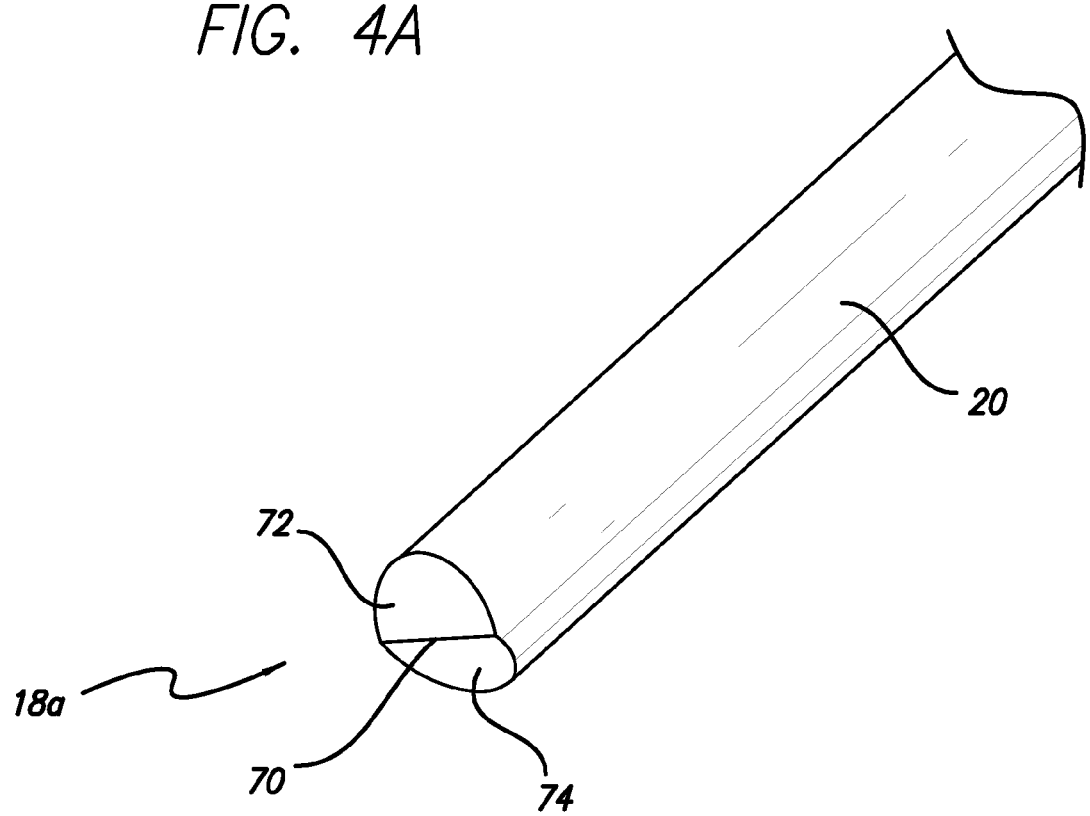
FIG. 4b is a perspective view of another embodiment of the tip.
Figure 4C:
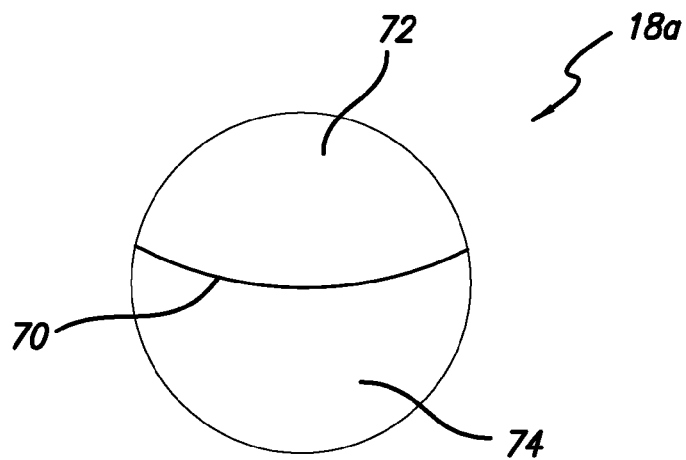
FIG. 4c is an end view of the tip of FIG. 4b.
Figure 4D:
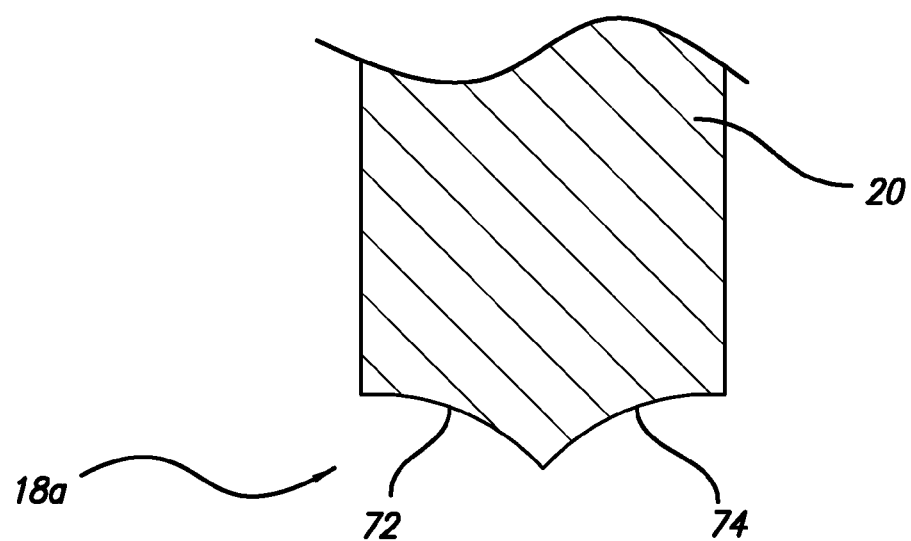
FIG. 4d is a cross-sectional side elevational view of the tip of FIG. 4b.

Referring to FIGS. 4b-4d, as will be appreciated by those skilled in the art, the cornea and sclera both have a different radius of curvature. As a result, an angle is formed where they join (see FIG. 2). As shown in FIGS. 4b-4c, in another embodiment, the tip 18a can be shaped so as to fit into or engage the junction of the cornea and sclera (known as the limbus). As shown in FIG. 4c, tip 18a includes a ridge 70, a corneal section 72 and a scleral section 74. The radius of curvature of the corneal section 72 and scleral section 74 mimics that of the typical cornea and sclera. As is shown in FIG. 4c, the ridge 70 has a slight curvature to it to match the natural curve of the cornea. In use, the ridge 70 is placed at the junction of the cornea and sclera (at the limbus) and the corneal section 72 rests against the cornea and the scleral section rests against the sclera. It will be understood that the ridge 70, corneal section 72 and scleral section 74 have smooth and rounded edges so as to prevent damage to the eye.

As shown in FIGS. 7-8, in another exemplary embodiment, the device is approximately 15 cm long from the tip to the base with an extension 19 of about 15 mm in length for connection to a power supply. In another embodiment, the device 10 can include a battery 13 or the like for power supply, which is also shown in FIG. 8. The diameter is approximately 3 cm at the widest and narrowing down to a polished flat tip 18 of approximately 2 mm in diameter. These dimensions are only exemplary and are not a limitation on the present invention.

In use, the ultrasonic energy produced by the transducer 14 is transmitted down the rod 20 and to the tip 18. As shown in FIGS. 7-8, in this embodiment, the rod is cone shaped. However, this is not a limitation on the present invention. Any shape is within the scope of the invention.

In another embodiment, the device can be miniaturized for ease of use. Any ultrasonic transducer that allows the method described herein to be performed at the desired parameters is within the scope of the present invention.

In an alternative embodiment, the tip may include a heating element that allows the heat created by the ultrasound energy to be enhanced. As is known in the art, tissue necrosis and pain are initiated at approximately 42.5 degrees centigrade. As is mentioned above, it is desirable to heat the target tissue enough to cause favorable biochemical processes. Accordingly, the heating element can be provided to heat the tissue to a level favorable to provide the biochemical processes described above, but below a level that creates tissue necrosis and pain. In an embodiment of the method, the temperature elevation may exceed 42.5 up to just below 45 degrees with a feeling of warmth and tingling but not pain. In another embodiment, the temperature could be elevated to above 45 degrees. Preferably, the temperature is between about 41 and about 45 degrees centigrade.

Figure 1:
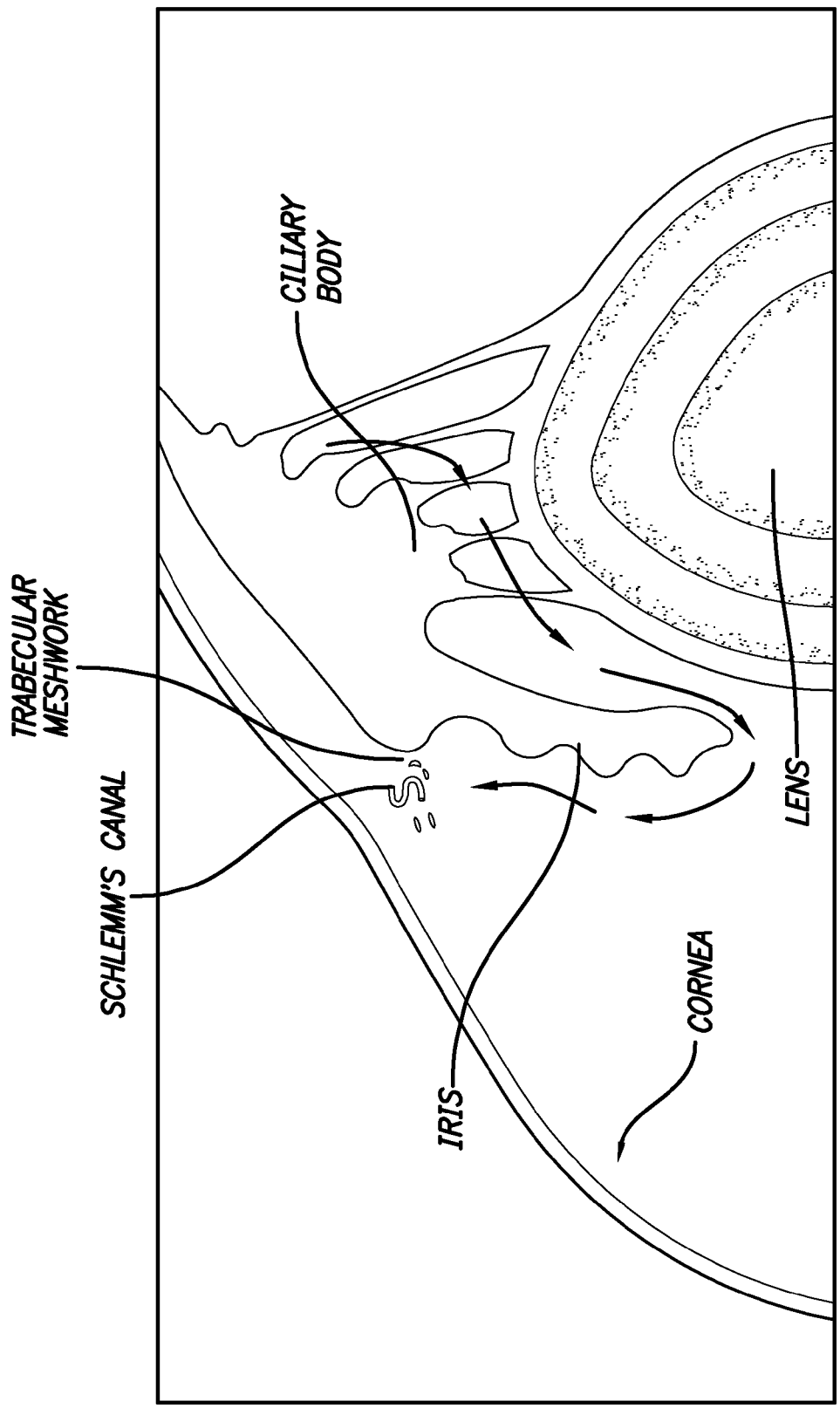
FIG. 1 is a view of a portion of the inside of an eye.

With reference to FIGS. 1 and 2 for the anatomy of the eye and FIG. 8, in use, the device 10 is used to apply directed or focused ultrasound to the area overlying the meshwork. In a preferred embodiment, the focal point of the ultrasonic energy is located within about 1 mm of the tip to avoid deeper effects. However, the focal point can be located at a point greater than or less than 1 mm from the tip. For example, the focal point can be 2 mm from the tip. In a preferred embodiment, the focal point is between about 0.001 mm from the tip and about 3.0 mm from the tip. In a more preferred embodiment, the focal point is between about 0.5 mm and about 2.0 mm from the tip. In a most preferred embodiment, the focal point is between about 0.75 mm from the tip and 1.25 mm from the tip. In another embodiment, the ultrasonic energy may be unfocused. For example, focused ultrasound can be applied at 63,500 Hz using 4 watts of power. As can be seen in FIG. 2, the meshwork is located near the area where the cornea and sclera meet. Preferably, anesthetic and/or conduction gel or liquid is placed on the eye (or on the tip 18) and then ultrasonic acoustic energy is applied at the desired frequency, which in turn is transmitted to the trabecular meshwork, thereby dislodging material that is blocking fluid passage and heating the meshwork to initiate heat shock proteins, stimulate matrix metalloproteinase and induce macrophage activity and/or other desired biochemical processes to decrease the pressure.

In operation, the device 10 is moved 360° around the eye over the limbal area, while providing ultrasonic energy to the eye. However, in a preferred embodiment, the tip 18 is not swept around the limbal area of the eye in a 360° path, but instead, the user stops at a number of predetermined points and applies the ultrasonic energy at a predetermined frequency, for a predetermined duration and at a predetermined power. For example, the user may stop at twelve equally spaced points similar to the hours on a clock. In another embodiment, with an approximately 4 mm tip, only eight treatment areas may be sufficient. Fewer than eight treatment areas and as few as one treatment area or more than twelve treatment areas can also be used. For example, a patient's anatomy may prevent the placement at twelve treatment areas and may only allow for six treatment areas.

The length of time, the number of treatment areas and the intensity of the ultrasound energy depend on individual cases. In an exemplary embodiment, the procedure may be performed at about 40,000 Hz with 3 watts of power for about forty five second intervals at about twelve points around the eye. In other procedures, the number of treatment areas may decrease while the treatment time increases when compared to other procedures. Accordingly, none of these numbers are a limitation on the present invention. What is important is that the biochemical changes are triggered by the procedure. Also, in some cases it may be necessary that after such treatment that anterior corneal massage is performed to help flush aqueous humor though the meshwork to help clear the pathway.

In operation, the ultrasonic energy is provided as follows. In a preferred embodiment, the frequency range of the ultrasonic energy is about 10,000 to 500,000 Hz. In a more preferred embodiment, the frequency range is from about 30,000 to 100,000 Hz. In a most preferred embodiment, the frequency range is from about 35,000 to 45,000 Hz. In a preferred embodiment, the duration range is about 5 to about 120 seconds. In a more preferred embodiment, the duration range is about 25 to about 60 seconds and in a most preferred embodiment, the duration range is about 40 to about 50 seconds. In a preferred embodiment, power is provided in the range of about 1 to about 6 watts, with about 3 watts being most preferred. As is described above, these ranges will be different for individual cases and therefore, these are not a limitation on the present invention.

These ranges are low intensity enough to prevent damage to the eye. However, in a preferred embodiment, the ultrasonic energy applied to the structures of the eye generates heat and sonomechanical acoustic streaming or stable cavitation that is transmitted to the meshwork and helps dislodge the built up material, and initiates biochemical changes to restructure the extracellular matrix and induce macrophage activity as described above.

In a preferred embodiment, to prevent contamination or spread from one patient to another, the exposed tip 18 or 18*a* of the device 10 can be covered with a small finger cot or condom. With such a cover over the tip there is little or no decrease in the treatment temperature rise than when the treatment is performed without a condom or the like.

In an exemplary embodiment, a device with a round flat tip having a focal point 1 mm from the tip is used. The patient's eye is anesthetized with a topical anesthetic drop, such as tetracaine. The eye is then marked with a marking pen into quadrants near the limbus. Anesthetic ophthalmic gel is used to anesthetize the eye and to provide a contact gel for the ultrasound. The device is tuned to a level of about 3 watts/cm2 at a frequency of between about 39 KHz and about 41 KHz.

The device is placed at a position distal to the cornea allowing approximately 0.5 mm of sclera to be seen between the instrument tip and the cornea. The device is held at angle of approximately 45 degrees from the sclera with the tip aimed at the limbus. Pressure is then exerted on the globe so that the usual limbal curvature is flattened and the globe has a minimal amount of retropulsion. The instrument is applied in this manner for about 45 seconds. During the 45 seconds, it takes about 20 seconds to reach the maximum effect and then 25 more seconds for treatment. The 45 second application is then repeated. The number and positions of these applications is divided equally around the circumference of the eye into 12 clock hours. In controlled studies in which this method was performed, the inventor has found that a reduction of intraocular pressure not only occurs in the treated eye, but also in the contralateral (control) eye. Thus, the method provides a bilateral effect that results in systemic biochemical triggering of the integrins that then lead to the systemic absorption and bilateral cytokine effect.

Thus, by the application of the described focused ultrasound, the method results in the triggering of integrins, and preferably the elevation of the temperature within the treatment area to a level that begins a biochemical cytokine cascade over the meshwork, chamber angle and the ciliary body that is then absorbed systemically leading to a decrease in intraocular pressure in both eyes.

Figure 9:
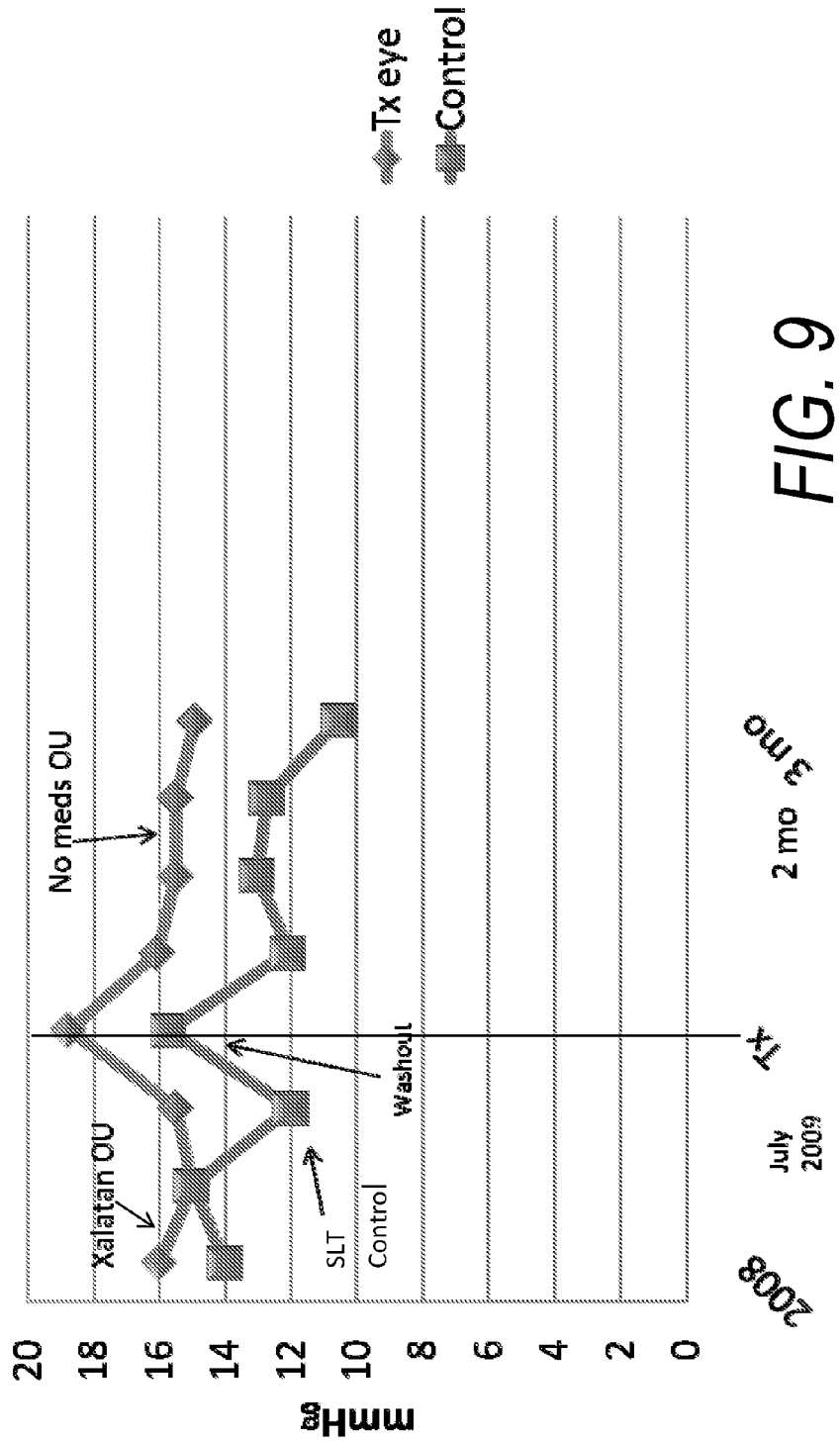
FIG. 9 is a graph showing an exemplary result of the performance of the method on a patient.

FIG. 9 is a graph that shows the results of the controlled use of the above-described method on a subject with glaucoma (subject #237). TUG stands for therapeutic ultrasound for glaucoma. The x-axis shows time and is not to scale. The y-axis shows intraocular pressure. The lines on the graph represent the treated eye (Tx) and the control eye (the subject's other eye, which was not treated with TUG directly). The TUG treatment was performed at the time represented by the vertical line Tx.

Prior to the TUG treatment, the subject was being treated for glaucoma in both eyes (OU) with the drug Xalatan (latanoprost) beginning in 2008. In addition, the subject had an SLT laser treatment on the control eye in July, 2009, which resulted in a drop in pressure in the treated control eye, but not in the other eye. Thereafter, there was a washout of the medication from both eyes for one month prior to the TUG treatment. During this washout period it can be see that the intraocular pressure rose in each eye.

The TUG treatment was then performed on the Tx eye and not on the control eye. Neither eye had medication after the TUG treatment (No meds OU). As shown in the graph, after TUG treatment, the intraocular pressure dropped in both eyes. Three months after treatment, the pressure continued to drop in both eyes, and, in the control eye, the pressure actually dropped below the lowest intraocular pressure level caused by the SLT laser treatment combined with medication.

Figure 6:
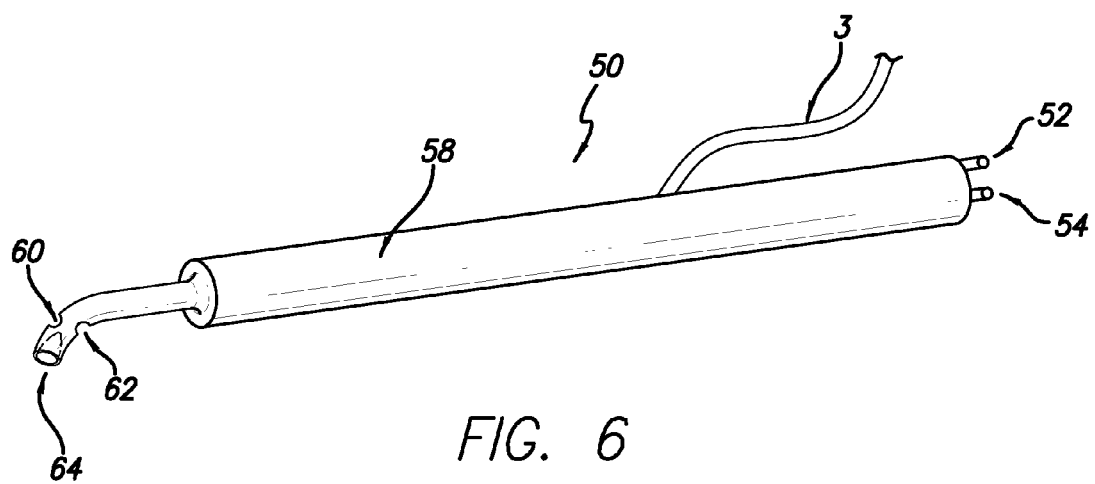
FIG. 6 is a side elevational view of an ultrasonic device used for treatment of glaucoma that is used intraocularly, in accordance with another preferred embodiment of the present invention.

Referring to FIG. 6, a device for treatment inside the eye is shown. This device is preferably used after cataract surgery since entry into the interior of the eye has already been made. However, this is not a limitation on the present invention. During cataract surgery the crystalline lens is replaced with an intraocular lens. The intraocular device 50 is for treatment within the eye. As described above, there is typically a decrease in pressure in the eye after cataract surgery.

The intraocular device 50 preferably includes attachment ports 52 and 54 for introduction of the irrigation fluid and aspiration of the irrigation fluid, respectively. However, it is contemplated that ports 52 and 54 can be omitted in an embodiment.

The intraocular device 50 also includes a power supply cord 56 for the transducer module (similar to the one in device 10) of the ultrasound, which is housed in a handpiece 58.

Located at an end of handpiece 58 opposite the end of attachment ports 54 and 56 is a tip 64 that preferably includes ports 60 and 62 that allow for the inflow of the fluid from attachment port 52 and into and out of the eye respectively.

The tip 64 is designed acoustically with the appropriate concavity or convexity to allow the focusing of the ultrasound into the trabecular meshwork. It may also be unfocused ultrasonic energy. In a preferred embodiment, the tip 64 includes an inverted cone tip that provides the ability to focus the ultrasonic energy and aim it into the anterior chamber angle. In one embodiment, the end of the tip 64 can be opened for irrigation, thereby eliminating the need for inflow port 60. In another embodiment the tip 64 may be solid to allow better ultrasonics. Preferably the tip 64 is not pointed to prevent unwanted damage to the intraocular lens or other parts of the interior of the eye.

In use, after the performance of cataract surgery and the replacement of the crystalline lens with an intraocular lens, the device 50 is used to apply ultrasonic energy into the anterior chamber angle, which is the area where the iris and cornea meet, and is directly above (as oriented in FIG. 2) the trabecular meshwork. Fluid is introduced as desired into the eye and then sonomechanical energy is transmitted to the trabecular meshwork using the device 50. The device 50 is held above the iris and intraocular lens (it preferably never contacts the iris or intraocular lens) and the ultrasonic energy is focused and directed at the anterior chamber angle, and then is moved to treat 360 degrees of the anterior chamber angle (similar to the description above with external device 10). The pulsed fluid wave vibrates the intratrabecular material free and flushes the meshwork. A coexisting aspiration port 62 allows dislodged material, such as pigment, pseudoexfoliative material, etc. in the anterior chamber to be removed.

One side effect of the method of ultrasonically vibrating the eye described herein is that the ultrasonic energy may change the vitreous gel in the back of the eye and allow vitreous detachment, i.e., separation of the vitreous gel from the retina. In addition, the use of ultrasound application by this device or of similar design may be used to trigger biochemical cascades which may be used to treat specific retinal diseases such as macular degenerative or developmental retinopathies. In this use, the focal point of the ultrasonic energy may be much greater than 3.0 mm from the tip, as described above. The focal point may reach to the back of the globe or all the way to the optic nerve, which can be 24-30 mm.

It will be understood that the use of the internal device 50 is similar to the external device 10 (including frequencies, durations, power, locations, etc.), except that the internal device is used inside the eye after an intraocular lens has been implanted. The treatment may be performed on a patient directly after implantation of the intraocular lens (or directly after cataract surgery) or it may be performed on a patient that had an intraocular lens at an earlier date.

The embodiments described above are exemplary embodiments of the present invention. Those skilled in the art may now make numerous uses of, and departures from, the above-described embodiments without departing from the inventive concepts disclosed herein. Accordingly, the present invention is to be defined solely by the scope of the following claims.

What is claimed is:

1. A method of treating glaucoma in a subject's eye that includes a cornea, a sclera, a limbus, a ciliary body and a trabecular meshwork, the method comprising the steps of:
    a. providing an ultrasonic device that emits focused ultrasonic energy;
    b. holding the ultrasonic device at a location external to the trabecular meshwork;
    c. transmitting the focused ultrasonic energy at a frequency to a desired location for a predetermined time; and
    d. increasing the temperature of a portion of the eye to a temperature of between about 41 and about 45 degrees centigrade to initiate a biochemical cascade within the eye, wherein the biochemicals reduce and remove extracellular debris from the trabecular meshwork.

2. The method of claim 1, wherein the device is held against the eye.

3. The method of claim 1, wherein the device has a tip, and wherein the tip includes a flat surface for contacting the eye.

4. The method of claim 1 wherein steps (a) through (d) are performed at a plurality of locations about the limbus.

5. The method of claim 1 wherein the frequency is between about 20,000 Hertz and about 100,000 Hertz.

6. The method of claim 5 wherein the time is between about 5 seconds and about 120 seconds.

7. The method of claim 1 wherein step (d) initiates heat shock proteins, stimulates matrix metalloproteinase and/or induces macrophage activity.

8. The method of claim 1 wherein step (d) includes increasing the temperature of a portion of the eye to cause an inflammatory reaction, wherein the inflammatory reaction initiates the biochemical cascade within the eye.

9. A method of treating glaucoma in a subject's eye that includes a cornea, a sclera, a limbus, a ciliary body and a trabecular meshwork, the method comprising the steps of:
    a. providing an ultrasonic device that emits focused ultrasonic energy;
    b. holding the ultrasonic device at a location external to the trabecular meshwork;
    c. transmitting the focused ultrasonic energy at a frequency to a desired location for a predetermined time; and
    d. increasing the temperature of a portion of the eye to initiate a biochemical cascade within the eye, wherein the biochemicals reduce and remove extracellular debris from the trabecular meshwork, and wherein the biochemical cascade includes the release of cytokines.

10. The method of claim 1 wherein the ultrasonic energy is focused at a point between about 0.5 mm and about 2.0 mm from a tip of the device.

11. The method of claim 9 wherein the release of cytokines causes a reduction in intraocular pressure in the eye.

12. The method of claim 11 wherein the release of cytokines causes a reduction in intraocular pressure in the subject's other eye.

* * * * *